(12) United States Patent
Cantin

(10) Patent No.: US 6,395,301 B1
(45) Date of Patent: May 28, 2002

(54) ANHYDROUS HYDROPHOBIC COSMETIC COMPOSITION IN THE FORM OF A COMPACT POWDER

(75) Inventor: Hervé Cantin, Morangis (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 09/476,784

(22) Filed: Dec. 30, 1999

(30) Foreign Application Priority Data

Dec. 30, 1998 (FR) .............................. 98 16662

(51) Int. Cl.$^7$ .............................. A61K 6/00; A61K 7/00; A61K 9/50; A61K 9/14; A61K 31/74; A61K 33/00; A61K 33/32; A61K 33/22; A61K 33/10; A01N 59/00; A01N 59/16; A01N 59/14; A01N 59/06; A46B 11/00

(52) U.S. Cl. ................. 424/489; 424/401; 424/502; 424/78.03; 424/600; 424/642; 424/657; 424/686; 424/687; 424/714; 514/844; 401/126; D28/78; 206/581

(58) Field of Search .............. 424/401, 78.03, 424/489, 502, 600, 642, 657, 686, 687, 715; 514/844, 952; 401/126; D28/78; 206/581

(56) References Cited

U.S. PATENT DOCUMENTS 5,073,364 A   12/1991   Giezendanner et al. ........ 424/63
5,518,728 A   5/1996   Burdzy ........................ 424/401
5,814,311 A * 9/1998   Le Bras-Roulier et al. ... 424/69

FOREIGN PATENT DOCUMENTS

EP   0534823 A1     3/1993
EP   0792633 A1 *   1/1997

OTHER PUBLICATIONS

D.F. Williams, "Chemistry and Technology of the Cosmetics and Tolietries Industry, Second Edition," Blackie Academic & Professional XP002116221, pp. 162–165.

English language Derwent abstract of EP0534823A1.

* cited by examiner

Primary Examiner—Dameron L. Jones
Assistant Examiner—Lauren Q. Wells
(74) Attorney, Agent, or Firm—Finnegan Henderson Farabow Garrett & Dunner, L.L.P.

(57) ABSTRACT

An anhydrous hydrophobic cosmetic composition in the form of a compact powder which can be taken up in dry form or with water, comprising a particulate phase comprising hydrophilic pulverulent compounds, wherein the hydrophilic pulverulent compounds represent 20 to 35% by weight relative to the total weight of the particulate phase. The invention also relates to a make-up process using such a composition, as well as to a device comprising such a composition and a sponge which can be moistened.

27 Claims, No Drawings

ANHYDROUS HYDROPHOBIC COSMETIC COMPOSITION IN THE FORM OF A COMPACT POWDER

The present invention relates to "two-way cakes," that is, cosmetic compositions in the form of powders, which can be used in either a dry form, as they are, or with water, by means of a damp sponge.

"Two-way cakes" are specific cosmetic powders in the form of compacted products and have the advantage of being able to be taken up with a dry sponge or a dry applicator, in which case they are used as conventional powders, or with water using a damp sponge, in which case they are used as foundations. Such products are particularly appreciated by consumers. Specifically, they are practical, compact, easy to use, and allow a double use, both as a powder and as a foundation, and yet only take up the space of a single product. When applied dry, they afford a sensation of softness and do not feel greasy. When applied wet, they afford a sensation of freshness.

The composition of "two-way cakes" is that of conventional powders. "Two-way cakes" thus generally comprise from 75 to 99% of pulverulent compounds and from 1 to 25% of binder, i.e., of oily compounds allowing cohesion of the pulverulent compounds.

However, since "two-way cakes" must be able to be taken up with a damp sponge, they must be hydrophobic. In fact, if this was not the case, the water in the damp sponge would be incorporated into the "two-way cake," the sponge would stick to the product, and it would be impossible to de-cake that part of the product in order then to apply it onto the face, for example. The expression "hydrophobic product" refers here to a product which does not incorporate or absorb a drop of water placed on its surface; the drop of water rolls over the surface. Most of the known "two-way cakes" are products which comprise only hydrophobic fillers and oils. They are thus completely hydrophobic.

However, the pulverulent compounds used in powders are not all naturally hydrophobic. Thus, compounds which are naturally hydrophobic and compounds which have been made hydrophobic by means of a specific coating, usually with a silicone, an amino acid or polyethylene, are conventionally incorporated in "two-way cakes." A product which contains only hydrophobic pulverulent compounds is thus obtained. The drawback of these products is that they are expensive and difficult to manufacture. The reason for this is that the coating of a pulverulent compound is a long and expensive operation.

The Inventor has now found, surprisingly, that it is possible to prepare cost effective "two-way cakes" which are easy to manufacture and which exhibit excellent cosmetic properties and properties of staying power over time, by selecting a specific type of hydrophilic pulverulent compounds. This discovery forms the basis of the present invention.

The present invention thus relates to a "two-way cake," or alternatively, to an anhydrous hydrophobic cosmetic composition in the form of a compact powder which can be taken up either in dry form or with water, comprising a particulate phase comprising hydrophilic pulverulent compounds, wherein the hydrophilic pulverulent compounds are present in an amount ranging from 20 to 35% by weight relative to the total weight of the particulate phase.

The composition according to the invention is extremely simple to prepare and can be manufactured according to conventional methods for preparing cosmetic powders. Since the inventive compositions comprise little powder which has been made hydrophobic by means of a treatment, or even none at all, it is not expensive.

The composition according to the invention has excellent cosmetic properties, de-cakes easily both in dry form and with water, and spreads remarkably well on the skin. The composition according to the invention has a texture which feels extremely fine. Furthermore, once the make-up has been applied, the composition is just as fine. It thus appears to give the skin a naturally fine and soft texture. It is resistant to sweat and sebum, and has very good staying power without making the skin sticky or shiny, in particular on the nose or the forehead (T-zone). The composition according to the invention makes the complexion uniform.

The present invention also relates to a cosmetic process for making up or caring for the skin, in particular of the human body, or of the mucous membranes (for example, the lips or the inside of the lower eyelids), comprising application of the composition as defined above to the skin or the mucous membranes.

Other characteristics, aspects and advantages of the invention will become apparent upon reading the detailed description which follows.

The compositions of the invention are cosmetic powders. They can thus comprise up to 100% by weight, preferably from 77 to 99% by weight, of a particulate phase relative to the total weight of the composition. The particulate phase comprises pulverulent compounds usually used in the manufacture of cosmetic powders. The pulverulent compounds can be chosen from fillers, pigments, nacres, and/or mixtures thereof.

The term "fillers" should be understood as comprising colorless or white, inorganic or organic, lamellar or non-lamellar particles intended to give body or rigidity to the composition, and/or softness, a matte-effect and uniformity to the make-up. The term "pigments" should be understood as comprising white or colored, inorganic or organic particles intended to color and/or opacify the composition. The term "nacres" should be understood as comprising iridescent particles which reflect light.

The fillers can be present in the composition of the invention in an amount which can range from 0.1 to 99% by weight relative to the total weight of the composition.

Among these fillers which may be mentioned, for example, are inorganic silicates, such as mica. The mica can be chosen from muscovite, phlogopite, tiotite, sericite, lepidolite, paragonite, synthetic micas and mixtures thereof. Preferably, natural or synthetic sericite is used, for example in an amount ranging from 1 to 30% by weight relative to the total weight of the composition.

Another filler which may also be mentioned is talc, which can, for example, be used in an amount which can range from 1 to 85% by weight relative to the total weight of the composition.

Other fillers which may also be mentioned are silica, kaolin, Nylon powder, poly-β-alanine powder, polyethylene powder, TEFLON®, lauroyllysine, starch, boron nitride, bismuth oxychloride, tetrafluoroethylene polymer powders, polymethyl methacrylate powders, polyurethane powders, polystyrene powders, polyester powders, hollow microspheres such as EXPANCEL (Nobel Industrie), microsponges such as POLYTRAP (Dow Corning) and silicone resin microbeads (TOSPEARLS from the company Toshiba, for example), zinc oxide, titanium oxide, zirconium oxide, cerium oxide, precipitated calcium carbonate, magnesium carbonate and hydrocarbonate, hydroxyapatite, hollow silica microspheres (silica beads from the company Maprecos, for example), glass or ceramic microcapsules, metal soaps derived from organic carboxylic acids containing from 8 to 22 carbon atoms, preferably from 12 to 18 carbon atoms, for example zinc, magnesium or lithium stearate, zinc laurate or magnesium myristate, and/or mixtures thereof.

The fillers can also be present in the form of compounds of composite structure, such as, for example, fillers composed of several layers of different pulverulent materials. Mention may be made of $SiO_2/TiO_2/SiO_2$, $TiO_2/CeO_2/SiO_2$, and $TiO_2/ZnO/$talc compounds.

The pigments can be present in the composition of the invention at a content which can range from 0.01 to 30%, preferably from 0.1 to 5%, by weight relative to the total weight of the composition. They can be of any usual cosmetic or nanometric size.

Among the inorganic pigments and nanopigments which may be mentioned are titanium dioxides, zinc oxides, iron oxides or chromium oxides, nanotitanias and ferric blue.

Among the organic pigments which may be mentioned are carbon black and the lakes commonly used to give the lips and the skin a make-up effect, which include calcium, barium, aluminium or zirconium salts, acidic dyes such as halo acid, azo or anthraquinone dyes, pigments of D&C type, lakes based on cochineal carmine, and/or mixtures thereof.

The nacres, which can be present in the composition in a range from 0 to 50% by weight, can be chosen from nacreous pigments, such as mica coated with organic and/or inorganic pigments, such as titanium dioxide or bismuth oxychloride, titanium mica coated with organic and/or inorganic pigments, such as iron oxides, ferric blue or chromium oxide, and nacreous pigments based on bismuth oxychloride, and/or mixtures thereof.

These pulverulent compounds are naturally hydrophobic or hydrophilic. In order to determine whether, according to the invention, a pulverulent material is "hydrophobic" or "hydrophilic," the test defined below is carried out. A test tube with a diameter of 20 mm is filled with 20 ml of water and 2 grams of powder are poured into the tube without stirring. The behavior of the powder is observed for a maximum of 5 minutes. If the powder all remains at the surface, it is considered as being "hydrophobic." Otherwise, it is considered as being "hydrophilic".

The hydrophilic pulveruient compounds are present in the compositions according to the invention in a content ranging from 20 to 35% by weight relative to the total weight of the particulate phase. The remaining part of the particulate phase contains hydrophobic pulverulent compounds.

The hydrophilic pulverulent compounds can be naturally hydrophilic or may have been made hydrophilic.

The naturally hydrophilic compounds can be chosen, for example, from:
  micas, which are potassium aluminium silicates of varied composition, of natural origin, such as muscovite, phlogopite, lepidolite, biotite and sericite, or of synthetic origin,
  bismuth oxychloride,
  silicas, which can be in the form of flakes or spheres, such as the silica sold under the name "Silica Beads SB 700" by the company Miyoshi,
  hydrophilic polymer powders, which are of synthetic origin, such as polyacrylates, for example the product sold under the name "Micropearl M 100" by the company Matsumoto, acrylic polyamides such as those sold by the company Oris, polyurethanes such as the product sold under the name "Plastic Powder D 800" by the company Toshnu, and cellulose or starch derivatives, for example hollow cellulose microspheres,
  kaolin, which is a hydrated aluminium silicate,
  hydroxyapatite,
  zinc oxide or titanium oxide, for their covering power in particular, it being possible for these products to be used in nanopigment form for their screening effect,
  calcium carbonate,
  magnesium carbonate and hydrocarbonate, which facilitate the binding of fragrances,
  and/or mixtures thereof.

The hydrophilic pulverulent compounds can also be pulverulent compounds which have been made hydrophilic by chemical grafting or coating with the aid of materials such as chitosan, titanium dioxide, silica or hydrophilic polymers, in particular sulphonic polyesters or polyquaternary ammoniums, and/or mixtures thereof.

Thus, the hydrophilic pulverulent compounds can be chosen from hydrophilic treated and/or coated talcs, hydrophilic treated and/or coated polyamide powders, hydrophilic treated and/or coated polyethylene powders, hydrophilic treated and/or coated powders of expanded copolymer of vinylidene chloride, acrylonitrile and methyl (meth)acrylate, hydrophilic treated and/or coated polyfluoro powders, hydrophilic treated and/or coated silicone powders, hydrophilic treated and/or coated acrylic copolymer powders, hydrophilic treated and/or coated polystyrene powders, hydrophilic treated and/or coated pigments, and/or mixtures thereof.

Examples of hydrophilic pulverulent compounds which may be mentioned are talc coated with chitosan, sold by Daito under the name "Talc CT 2 MSA," and mica coated with silica microspheres, sold by Catalysts and Chemicals under the name "Cashmir B3."

The hydrophilic pulverulent compounds can also be chosen from organic or inorganic hydrophilic pigments which can be used cosmetically.

Among the inorganic pigments which may be mentioned, in particular, are:
  the black, yellow, red and brown iron oxides listed in the Color Index under the references CI 77499, CI 77492 and CI 77491,
  manganese violet (CI 77742),
  ultramarine blue (CI 77007),
  ultramarine violet (CI 77007),
  chromium oxide (CI 77288),
  hydrated chromium oxide (CI 77289), and
  ferric blue (CI 77510),
  and/or mixtures thereof.

Among the organic pigments which may be mentioned in particular are the following pigments:
  pigments of the D & C type, for example:
    D & C red No. 3 (CI 45430:1),
    D & C red No. 6 (CI 15850:2),
    D & C red No. 7 (CI 15850:1),
    D & C red No. 9 (CI 15585:1),
    D & C red No. 13 (CI 15630:3),
    D & C red No. 19 (CI 45170),
    D & C red No. 21 (CI 45380:2),
    D & C red No. 27 (CI 45410:1),
    D & C red No. 30 (CI 73360),
    D & C red No. 36 (CI 12085), carbon black (CI 77266) and lakes based on cochineal carmine (CI 75470),
  and/or mixtures thereof.

The hydrophobic pulverulent compounds can be chosen from pulverulent compounds which are hydrophobic by nature, such as, for example:

talc, which is a hydrated magnesium silicate, hydrophobic polymer powders, such as polyamide powders of Nylon type, for example the product sold under the name "Orgasol 2002 ED NAT COS" by the company Atochem; polyethylene powder, for example the product sold under the name "Coathylene HA 1681" by the company Plast Labor; expanded microspheres made of thermoplastic material, for example the product sold under the name "Expancel 551 DE" by the company Casco-Nobel; polyfluoro powders, in particular polytetrafluoroethylene powder, for example the product sold under the name "MP 1400" by the company Dupont de Nemours; silicone powders, for example the products sold under the name "Tospearl" by the company Toshiba; acrylic copolymer powders, such as the products sold under the name "Polytrap Q56603" by the company Dow Chemica; and polystyrene powders such as the products sold under the name "Polysphere 3000 SP" by the company Presperese;

lipoamino acids, for example lauroyllysine, boron nitride, metal soaps of $C_8$–$C_{22}$, more particularly $C_{12}$–$C_{18}$, carboxylic acids, for example zinc and magnesium stearates, zinc laurate or magnesium myristate, and/or mixtures thereof.

The hydrophobic pulverulent compounds can also be chosen from pulverulent compounds which are either of hydrophobic or hydrophilic nature which have been made hydrophobic by treating them, by chemical grafting or coating, with products such as silicones, amino acids, metal soaps, fluoro derivatives, mineral oils, lecithin, isopropyl triisostearoyl titanate, polyethylene, collagen and derivatives thereof, polyacrylates and/or mixtures thereof.

Thus, the hydrophobic pulverulent compounds can be chosen from hydrophobic coated and/or treated micas, hydrophobic coated and/or treated silicas, hydrophobic coated and/or treated kaolin, hydrophobic coated and/or treated metal oxides such as hydrophobic coated and/or treated titanium oxides, hydrophobic coated and/or treated iron oxides, and hydrophobic coated and/or treated zinc oxides, and/or mixtures thereof.

Examples of hydrophobic pulverulent compounds which may be mentioned are silica microbeads coated with polymethylhydrogenosiloxane, sold under the trade name "Silica SI SB 700" by Miyoshi or sericite coated with methicone/hydrogenated egg oil, sold under the trade name "Sericite SNI S100" by Miyoshi.

The compositions according to the invention can also comprise a fatty phase, as a binder comprising fatty substances, which facilitates the adhesion of the pulverulent compounds to the skin and their cohesion with each other in the final composition. These fatty substances can be chosen from oils and/or waxes of mineral, animal or plant origin, silicone oils, fluoro oils, fatty acid esters and/or mixtures thereof.

Among the oils Which can be used, mention may be made of mink oil, turtle oil, soybean oil, grape seed oil, sesame oil, corn oil, rapeseed oil, sunflower oil, cotton oil, avocado oil, olive oil, castor oil, jojoba oil, and groundnut oil; hydrocarbon oils such as liquid paraffin, squalane and petroleum jelly; fatty esters such as isopropyl myristate, isopropyl palmitate, butyl stearate, hexyl laurate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl and diglyceryl triisostearate; silicone oils such as polymethylsiloxanes, polymethylphenylsiloxanes, polysiloxanes modified with fatty acids, with fatty alcohols or with polyoxyalkylenes, fluorosilicones, and perfluoro oils; higher fatty acids such as myristic acid, palmitic acid, stearic acid, behenic acid, oleic acid, linoleic acid, linolenic acid and isostearic acid; higher fatty alcohols such as cetanol, stearyl alcohol or oleyl alcohol, and/or mixtures thereof.

Preferably, silicone oils such as polymethylsiloxanes, polymethylphenylsiloxanes and/or mixtures thereof will be chosen.

Among the waxes which can be used, mention may be made of beeswaxes, lanolin waxes and Chinese insect waxes, carnauba wax, candelilla wax, ouricury wax, cork fibre waxes, sugar cane waxes, Japan waxes, hydrogenated jojoba waxes and hydrogenated oils such as hydrogenated sunflower oil, hydrogenated castor oil, hydrogenated coconut oil and hydrogenated lanolin; paraffins, microcrystalline waxes, montan waxes and ozokerites; polyethylene waxes, waxes obtained by Fischer-Tropsch synthesis, waxy copolymers and esters thereof, and silicone waxes such as polyalkoxysiloxanes and polyalkylsiloxanes, and/or mixtures thereof.

The fatty phase can also comprise silicone resins.

The fatty phase is preferably present in the compositions according to the invention in an amount which can range from 0.1 to 25% by weight, preferably from 3 to 15%, relative to the total weight of the composition.

The fatty phase can also comprise additives such as lipophilic cosmetic active agents and/or liposoluble ingredients generally used in cosmetics, such as fragrances and sunscreens. Preferably, these additives can be present in a proportion ranging from 20 to 70% by weight relative to the total weight of the fatty phase.

The composition of the invention can also comprise any additive usually used in the cosmetics field, such as, for example, antioxidants, essential oils, preserving agents, neutralizing agents, water-in-oil (W/O) or oil-in-water (O/W) surfactants, vitamins, anti-wrinkle active agents, and/or mixtures thereof.

The compositions according to the invention are in the form of compact or pressed powder. They are hydrophobic and anhydrous. The term "anhydrous" means a composition which is substantially free of water, preferably a composition in which water is present at a content of less than or equal to 2% by weight relative to the total weight of the composition.

The compositions according to the invention are prepared according to conventional methods for preparing compact or pressed powders. The pulverulent compounds are mixed. The fatty phase is then added dropwise and mixing is again carried out. The mixture obtained is then ground, after which it is screened to deaggregate the mixture. The powder is then compacted in a dish.

The compositions according to the invention can be used either in dry form or with water. When they are used in dry form, they can be taken up with the fingers or with a sponge or a dry applicator. In this case, they are used as powders, for example over a moisturizing cream or a foundation. They then afford a sensation of softness and do not feel greasy. They give the skin a velvety, airy appearance.

The compositions can also be used with water by means of an applicator which has been moistened beforehand and with which some of the powder is de-caked. This powder is mixed with the water and the composition is then used on the skin as a foundation. It thus affords a sensation of freshness and gives the skin a matte effect, excellent coverage, and unifies the complexion.

The same applicator can be suitable for the two uses of the compositions of the invention. This applicator must be capable of being moistened. It can be, for example, a sponge or an applicator made of one or more materials of natural or synthetic origin, such as, for example, polyurethane, polyester, polyether, polyvinyl chloride or polyethylene foams. It is chosen for its cosmetic qualities such as softness and thickness. It is neither too rigid nor too soft. Preferably, the applicator is a sponge made of polymer of medium-density NBR type.

A subject of the present invention is also a device comprising a composition as described above and an applicator which can be moistened, preferably a sponge.

The invention is illustrated in greater detail in the examples which follow, which are not intended to be limiting. The percentages are given on a weight basis relative to the total weight of the composition.

EXAMPLE 1

Inventive

The Inventor prepared a two-way cake in accordance with the invention below:

| Phase A | |
|---|---|
| -hydrophobic talc | 47.1% |
| Phase B | |
| -hydrophilic iron oxide | 0.8% |
| -hydrophilic iron oxide | 0.8% |
| -hydrophilic iron oxide | 0.3% |
| -hydrophilic mica | 20% |
| -hydrophilic titanium dioxide | 5% |
| -hydrophobic Nylon | 10% |
| -hydrophobic zinc laurate | 5% |
| -hydrophobic lauroyllysine | 2.7% |
| -hydrophilic paraben | 0.3% |
| Phase C | |
| hydrophobic binder | 8% |

This composition was prepared by mixing phase A and phase B together, followed by addition of phase C. The mixture obtained was then ground, screened, and then compacted.

This composition comprised 29.5% by weight of hydrophilic pulverulent compounds, relative to the weight of the particulate phase. It was hydrophobic, and could be used in dry form or with water. It comprised few coated fillers and was consequently very inexpensive and very simple to manufacture. It de-caked easily with a damp sponge or a dry sponge.

EXAMPLE 2

Comparative

The Inventor prepared the following comparative composition:

| Phase A: | |
|---|---|
| -hydrophobic talc | 36.6% |
| Phase B: | |
| -hydrophilic pigments | 1.6% |
| -hydrophobic Nylon powder | 20% |
| -hydrophilic magnesia | 1.8% |
| -hydrophilic bismuth oxychloride | 10% |
| -hydrophobic zinc stearate | 4% |
| -hydrophilic mica | 20% |
| Phase C: | |
| -hydrophobic binder | 6% |

This composition was prepared in the same way as the composition of Example 1. It comprised 35.5% by weight of hydrophilic pulverulent compounds, relative to the weight of the particulate phase. When an attempt was made to take up some of the powder using a damp or moistened sponge, unusable powder aggregates formed on the sponge. It was not possible to de-cake such a composition for a cosmetic application on the face.

What is claimed is:

1. An anhydrous hydrophobic cosmetic composition in the form of a compact powder, said composition comprising a particulate phase comprising hydrophilic pulverulent compounds, wherein the hydrophilic pulverulent compounds are present in an amount ranging from 20 to 35% by weight relative to the total weight of the particulate phase.

2. A composition according to claim 1, wherein the composition is substantially free of water.

3. A composition according to claim 2, wherein water is present in an amount of less than or equal to 2% by weight relative to the total weight of the composition.

4. A composition according to claim 1, wherein the particulate phase is present in an amount ranging from 77 to 99% by weight relative to the total weight of the composition.

5. A composition according to claim 4, wherein the particulate phase comprises pulverulent compounds chosen from fillers, pigments, nacres, and mixtures thereof.

6. A composition according to claim 5, wherein the fillers are present in an amount ranging from 0.1 to 99% by weight relative to the total weight of the composition.

7. A composition according to claim 6, wherein the fillers are chosen from mica, talc, silica, kaolin, Nylon powder, poly-β-alanine powder, polyethylene powder, Teflon, lauroyllysine, starch, boron nitride, bismuth oxychloride, tetrafluoroethylene polymer powders, polymethyl methacrylate powders, polyurethane powders, polystyrene powders, polyester powders, hollow microspheres, silicone resin microsponges and microbeads, zinc oxide, titanium oxide, zirconium oxide, cerium oxide, precipitated calcium carbonate, magnesium carbonate and hydrocarbonate, hydroxyapatite, hollow silica microspheres, glass or ceramic microcapsules, metal soaps derived from organic carboxylic acids containing from 8 to 22 carbon atoms, and mixtures thereof.

8. A composition according to claim 7, wherein the metal soaps derived from organic carboxylic acids contain from 12 to 18 carbon atoms.

9. A composition according to claim 8, wherein the metal soaps are chosen from zinc, magnesium or lithium stearate, zinc laurate, magnesium myristate, and mixtures thereof.

10. A composition according to claim 7, said composition comprising from 1 to 85% by weight of talc relative to the total weight of the composition.

11. A composition according to claim 7, said composition comprising from 1 to 30% by weight of mica chosen from natural or synthetic sericite relative to the total weight of the composition.

12. A composition according to claim 5, wherein the pigments are present in an amount ranging from 0.01% to 30% by weight relative to the total weight of the composition.

13. A composition according to claim 12, wherein the pigments are present in an amount ranging from 0.1% to 5% by weight relative to the total weight of the composition.

14. A composition according to claim 12, wherein the pigments are chosen from titanium dioxides, zinc oxides, iron oxides, chromium oxides, nanotitanias, ferric blue, carbon black, calcium, barium, aluminium or zirconium salts, acidic dyes, azo or anthraquinone dyes, D&C pigments, cochineal carmine lakes, and mixtures thereof.

15. A composition according to claim 5, wherein the nacres are present in an amount ranging up to 50% by weight relative to the total weight of the composition.

16. A composition according to claim 1, wherein the hydrophilic pulverulent compounds are chosen from micas of natural origin, micas of synthetic origin, bismuth oxychloride, silicas, hydrophilic polymer powders, acrylic polyamides, polyurethanes, celluloses, starches, kaolin, hydroxyapatite, zinc oxides, titanium oxides, calcium carbonate, magnesium carbonates and hydrocarbonates, pulverulent compounds made hydrophilic by chemical grafting or coating, and mixtures thereof.

17. A composition according to claim 16, wherein the micas of natural origin are chosen from muscovite, phlogopite, lepidolite, biotite, sericite, and mixtures thereof.

18. A composition according to claim 16, wherein the pulverulent compounds made hydrophilic by chemical grafting or coating are made hydrophilic with chitosan, titanium dioxide, silica, hydrophilic polymers, or mixtures thereof.

19. A composition according to claim 18, wherein the hydrophilic polymers are chosen from sulphonic polyesters, polyquaternary ammoniums, hydrophilic pigments, and mixtures thereof.

20. A composition according to claim 1, further comprising a fatty phase.

21. A composition according to claim 20, wherein the fatty phase represents from 0.1 to 25% of the composition.

22. A composition according to claim 21, wherein the fatty phase represents from 3 to 15% of the composition.

23. A composition according to claim 20, wherein the fatty phase comprises oils chosen from polymethylsiloxanes, polymethylphenylsiloxanes, and mixtures thereof.

24. A composition according to claim 1, further comprising an additive chosen from antioxidants, essential oils, preserving agents, neutralizing agents, water-in-oil or oil-in-water surfactants, vitamins, anti-wrinkle agents, and mixtures thereof.

25. A method for making up or caring for the skin or the mucous membranes, said method comprising applying to the skin or the mucous membranes an effective amount of an anhydrous hydrophobic cosmetic composition in the form of a compact powder, said composition comprising a particulate phase comprising hydrophilic pulverulent compounds, wherein the hydrophilic pulverulent compounds are present in an amount ranging from 20 to 35% by weight relative to the total weight of the particulate phase.

26. A device comprising an anhydrous hydrophobic cosmetic composition in the form of a compact powder, said composition comprising a particulate phase comprising hydrophilic pulverulent compounds, wherein the hydrophilic pulverulent compounds are present in an amount ranging from 20 to 35% by weight relative to the total weight of the particulate phase, and an applicator which can be moistened.

27. A device according to claim 26, wherein the applicator is a sponge.

* * * * *